United States Patent
Kuwahara

(10) Patent No.: US 6,576,902 B2
(45) Date of Patent: Jun. 10, 2003

(54) CORRECTION METHOD OF SCANNING ELECTRON MICROSCOPE

(75) Inventor: Kazuyuki Kuwahara, Tokyo (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 217 days.

(21) Appl. No.: 09/734,556

(22) Filed: Dec. 13, 2000

(65) Prior Publication Data

US 2002/0008200 A1 Jan. 24, 2002

(30) Foreign Application Priority Data

Jul. 21, 2000 (JP) .................................... 2000-221252

(51) Int. Cl.$^7$ ............................................... H01J 37/26
(52) U.S. Cl. ................ 250/310; 250/306; 250/307; 250/311; 250/492.2; 250/442.11; 250/398
(58) Field of Search ............................ 250/310, 306, 250/307, 311, 492.2, 442.11, 398

(56) References Cited

U.S. PATENT DOCUMENTS

| | | | |
|---|---|---|---|
| 4,763,004 A | 8/1988 | Yasuda et al. | 250/396 R |
| 5,387,799 A | 2/1995 | Sohda et al. | 250/492.2 |
| 5,512,747 A | 4/1996 | Maeda | 250/310 |
| 5,552,602 A | 9/1996 | Kakibayashi et al. | 250/311 |
| 5,578,821 A | * 11/1996 | Meisberger et al. | 250/310 |
| 5,929,439 A | * 7/1999 | Todokoro et al. | 250/310 |

* cited by examiner

Primary Examiner—John R. Lee
Assistant Examiner—Nikita Wells
(74) Attorney, Agent, or Firm—Rabin & Berdo, P.C.

(57) ABSTRACT

A method of correcting a scanning electron microscope using a detection sample for producing light of an intensity corresponding to an electron density of an electron beam irradiating a surface of the detection sample. Precise correction of the scanning electron microscope is performed on the basis of the intensity of the light generated on the detection sample.

13 Claims, 6 Drawing Sheets

F I G. 1
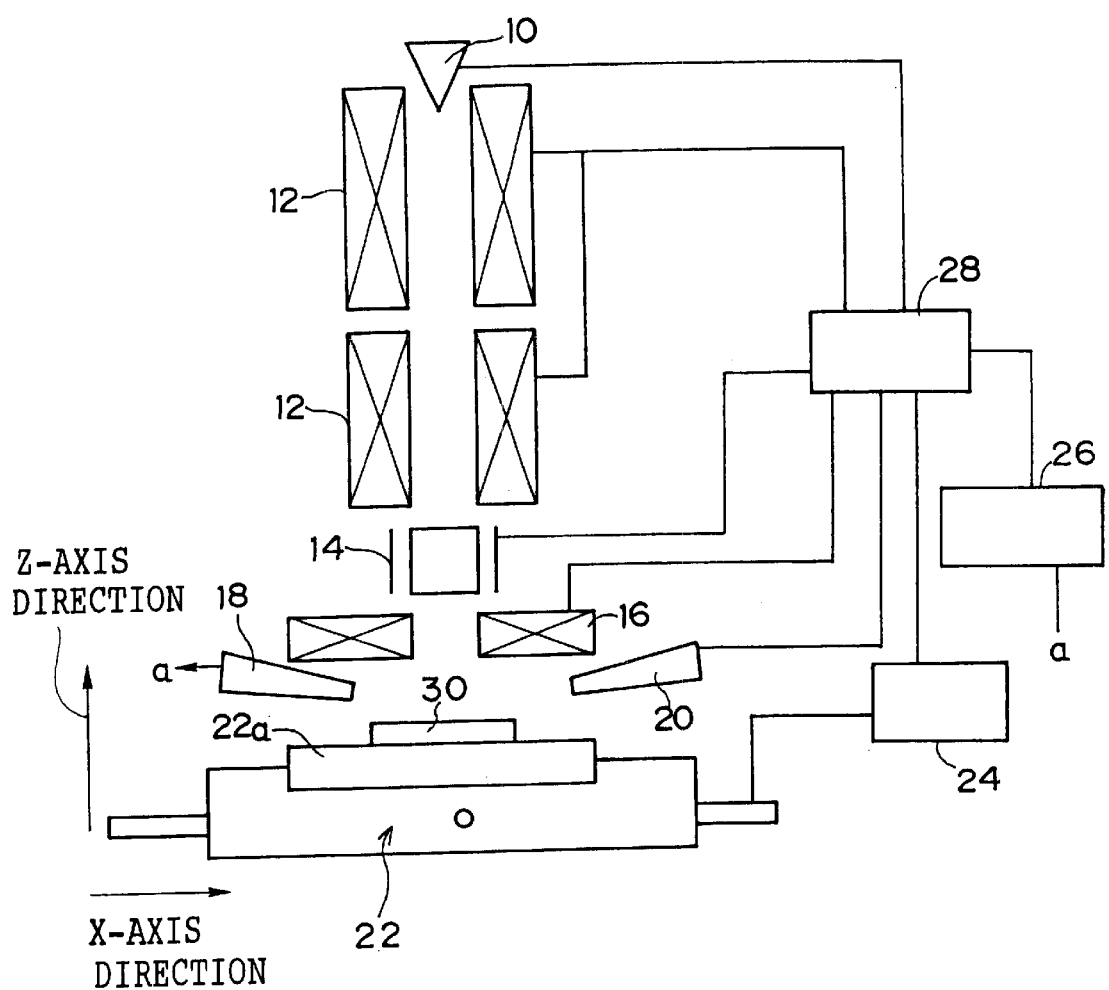

CORRECTION METHOD OF SCANNING ELECTRON MICROSCOPE

BACKGROUND OF THE INVENTION

1. Field of Invention

The present invention relates to a correction method of a scanning electron microscope. In particular, the present invention relates to a correction method of a scanning electron microscope employed for dimensional measurement or the like of a highly integrated circuit semiconductor.

2. Description of the Related Art

Currently, measurement of pattern dimensions in a semiconductor device is performed by a scanning electron microscope (hereinafter, SEM). This SEM is an apparatus for observing a surface of a micro (minute) sample by scanning an electron beam on the surface of the minute sample instead of light. The SEM has a merit in that the sample can be observed in a wide range from scores of magnifications to hundreds of thousands of magnifications (the magnification in which a molecular level can be observed).

In general, in the SEM, an electron generated by an electron gun is converged to an electron beam by a group of electromagnetic lenses. This electron beam is adjusted by means of an electromagnetic lens for focal position control so as to be converged at one point on a stage. This electron beam is scanned on the stage in a two-dimensional manner by controlling a magnetic field caused by a beam-scanning electrode.

When a sample is placed on the stage, and irradiated by the electron beam, secondary electrons according to a rugged state of a sample surface are discharged from the sample surface targeted for measurement. In the SEM, the discharged secondary electrons are collected, and are detected by means of a detector such as a scintillator or a photo multiplier (photoelectric multiplier) to be electrically converted. The electrically converted electron is synchronized with a scan signal of a scanning radiation of a display section such as a CRT, whereby a secondary electron image (hereinafter, referred to as an SEM image) according to the rugged state of the sample surface is obtained. Since the scanning range of the electron beam is narrow, the stage is moved in a X-Y plane direction by means of a stage movement system, whereby the SEM image of the entire sample targeted for measurement is obtained.

In addition, the SEM enables observation of a minutely small region, and thus, it is used as an apparatus for dimensional measurement as well as sample observation. In this case, it is required to perform the correction work of dimensional measurement precision, thereby maintaining the measurement precision. Conventionally, for example, correction has been performed by obtaining how many dots on the screen the SEM image of a standard sample whose dimensions are obtained in advance correspond to.

Conventionally, it is presumed that the electron beams of the SEM are always converged at one point on the sample surface, and that an ideal irradiation position caused by an electron beam control signal coincides with an irradiation position of actual electron beam. However, it is not actually verified as to whether or not the electron beam is converged on the sample surface and as to whether or not the ideal irradiation position caused by the electron beam control signal coincides with the actual irradiation position of electron beams.

Because of this, actually, if the electron beam is not always converged at one point on the sample surface or if the ideal irradiation position of electron beam does not coincide with the irradiation position of actual electron beam, these cannot be detected. Thus, there is a problem that a displacement between an actual sample surface and a detected image occurs, and the detection precision is impaired.

In addition, since the ideal irradiation position caused by the electron beam control signal does not coincide with the actual irradiation position of the electron beam, the electron beam is not actually irradiates a user-specified irradiation position. That is, the electron beam is irradiates a different position. Thus, there is a problem that an SEM image at the irradiation position that is not specified by the user is recognized as an SEM image at the user-specified irradiation position.

SUMMARY OF THE INVENTION

From the foregoing, it is an object of the present invention to provide a method of correction of a scanning electron microscope capable of performing correction with high precision by causing the user-specified irradiation position of the electron beam to coincide with the actual irradiation position of the electron beam.

In order to achieve the foregoing object, according to a first aspect of the present invention, there is provided a scanning electron microscope correction method comprising the steps of: setting a detection sample for producing light of an intensity corresponding to an electron density of an electron beam irradiating a surface of the detection sample; irradiating with the electron beam a predetermined position of the detection sample placed on a movable stage of the scanning electron microscope; detecting the intensity of the light produced from the detection sample; and performing correction relating to the scanning electron microscope on the basis of the intensity of the detected light.

In the scanning electron microscope correction method according to the first aspect of the present invention, correction relevant to the scanning electron microscope is performed by, for example, utilizing the fact that the density of the electron beam irradiated to the surface of the detection sample is a maximum and the detected light intensity is a maximum when the focal position of the electron beam irradiating the detection sample is precisely converged on the surface of the detection sample. For example, at least one of the movement amount of the focal position of the electron beam and the movement amount of the stage is corrected.

In this way, for example, the user-specified focal position of the electron beam can coincide with an actual focal position of the electron beam accurately, and the focal position of the electron beam can be corrected with high precision.

A focal position can be corrected by correcting, for example, the movement amount of the focal position so that the detected light intensity is always a maximum at each of the different positions on the detection sample on an inactive stage or the movement amount of the stage so that the detected light intensity is always a maximum in a state in which the movement amount of the focal position is constant (fixed). In addition, the focal position is moved in an optical axial direction so that the detected light intensity during electron beam scanning is always a maximum, whereby the focal position can be corrected.

According to a second aspect of the present invention, there is provided a scanning electron microscope correction method, wherein one of a movement control amount of a focal position of the electron beam in an optical axis direction and a movement control amount of the stage in the optical axis direction is corrected at a plurality of positions on the stage. In this manner, the focal position is corrected corresponding to an inclination of the stage. Thus, the displacement of the focal position due to such inclination of the stage is prevented, and an error caused by the inclination of the stage can be eliminated.

First, an electron beam irradiates a predetermined position, and the movement control amount of the focal position in the optical axis direction is corrected. Then, the stage is moved, and the irradiation position of the electron beam is changed to another position, whereby the electron beam irradiates another position. If the stage is inclined, the focal position is shifted from the surface of the detection sample, and the maximum optical intensity is not obtained.

In order to maximize the light intensity, there can be employed a method of adjusting the movement control amount of the focal position in the optical axis direction at each position after the stage has been moved; and a method of adjusting the inclination of the stage at each position after the stage has been moved.

According to the former method, i.e., the method of adjusting the movement control amount of the focal position in the optical axis direction at each position after the stage has been moved, even if the stage is moved while it is inclined, the focal position is always on the detection sample. Thus, even if the stage is inclined, the sample can be well observed.

According to the latter method, i.e., the method of adjusting the inclination of the stage at each position after the stage has been moved, if the stage is not inclined, the focal position of the electron beam at each position is not shifted from the detection sample. Thus, the movement control amount of the focal position in the optical axis direction after the stage has been moved is set to zero. If the stage is inclined, the focal position of the electron beam at each position is shifted from the detection sample. Thus, the movement control amount of the focal position in the optical axis direction after the stage has been moved is not set to zero, which corresponds to the stage inclination quantity.

Therefore, the inclination of the stage is adjusted so that the movement control amount of the focal position in the optical axis direction after the stage has been moved is set to zero, whereby the stage is accurately set so that the inclination of the stage is eliminated when the initially corrected position is defined as a reference, thus enabling correction with high precision.

According to a third aspect of the present invention, there is provided a scanning electron microscope correction method according to the first or second aspects thereof, wherein the movement control amount of the stage in the optical axis direction and the movement control amount of the focal position of the electron beam in the optical axis direction are corrected on the basis of a correlation between a predetermined movement amount of the stage in the optical axis direction, and a movement amount of the focal position of the electron beam in the optical axis direction when the focal position of the electron beam is moved in the optical axis direction so that the light intensity is a maximum after the stage, in a state in which the focal position of the electron beam is set on the detection sample, has been moved in the optical axis direction by the predetermined movement amount.

When the stage is moved in the optical axis direction after the focal position has been corrected, the focal position is shifted from the detection sample. This displacement quantity corresponds to the actual movement amount of the stage in the optical axis direction. In addition, the displacement quantity corresponds to a distance that correlates with the movement amount (or the adjustment amount) of the focal position of the electron beam when the detected light is at the maximum light intensity after the stage has moved in the optical-axis direction.

According to the third aspect of the present invention, the movement control amount of the stage in the optical axis direction and the movement control amount of the focal position of the electron beam in the optical axis direction are corrected based on a correlation between the movement amount of the focal position of the electron beam in the optical axis direction and the movement amount of the stage in the optical axis direction. In this manner, actual movement of the stage in the optical axis direction can accurately coincide with movement of the focal position of the electron beam in the optical axis direction, thus enabling correction with high precision. The actual movement amount of the stage in the optical axis direction may be measured by employing a position detecting apparatus such as interference gauge.

According to a fourth aspect of the present invention, there is provided a scanning electron microscope correction method according to any of the first to third aspects thereof, wherein a plurality of detection samples are disposed on the stage at known intervals, and a movement control amount of the stage with respect to an actual movement amount of the stage is corrected on the basis of the movement control amount of the stage from a position at which the electron beam irradiates a first detection sample which is one of the plurality of detection samples to a position at which the electron beam irradiates a second detection sample which is another of the plurality of detection samples, at the time the stage is moved linearly such that the electron beam irradiates the first detection sample and the second detection sample, and on the basis of a distance between the first detection sample and the second detection sample.

According to a ninth aspect of the present invention, there is provided a scanning electron microscope correction method for two-dimensionally scanning an electron beam with respect to a sample, thereby two-dimensionally detecting secondary electrons irradiated from (emitted from or by) the sample and reading a secondary electron image, said method employing a plurality of detection samples, each the detection samples generating light of a predetermined intensity corresponding to an electron density of the electron beam irradiated onto a surface of respective detection samples, wherein the plurality of detection samples are disposed on the stage at known intervals, and a stage movement control amount with respect to an actual stage movement amount is corrected on the basis of a stage movement control amount from a position at which an electron beam irradiates a first detection sample which is one of a plurality of detection samples to a position at which an electron beam irradiates a second detection sample which is another of the plurality of detection samples, at the time the stage is moved linearly such that the electron beam irradiates the first detection sample and the second detection sample, and on the basis of a distance between the first detection sample and the second detection sample.

A plurality of detection samples is disposed on a stage with predetermined intervals. The stage is linearly moved so that an electron beam having its focal position corrected passes over two samples between a first detection sample and a second detection sample. The detection sample is disposed on the stage with the known intervals. Thus, the movement control amount of the stage (stage movement control amount) required for actually linearly moving the electron beam from the first detection sample to the second detection sample corresponds to a known distance between the first detection sample and the second detection sample. Here, the stage movement control amount can be obtained based on light generation in the first detection sample and light generation in the second detection sample.

Therefore, a unit movement control amount of the stage with respect to an actual unit movement distance of the stage can be accurately detected based on the known distance and the stage movement control amount, and thus, the stage movement control amount with respect to the actual stage movement amount can be corrected with high precision.

According to a fifth aspect of the present invention, there is provided a scanning electron microscope correction method according to any one of the first to fourth aspects thereof, wherein the detection sample is formed in a rectangular parallelepiped shape with a width that is almost equal to or smaller than a diameter of the electron beam in a transverse direction of the detection sample, and when the detection sample is placed on the stage and the electron beam irradiates the detection sample and one of that the electron beam is scanned or that the stage is moved is performed, at least one of a scanning direction of the electron beam or a movement direction of the stage is corrected so that a light detection time becomes the longest.

According to a tenth aspect of the present invention, there is provided a scanning electron microscope correction method for two-dimensionally scanning an electron beam with respect to a sample, thereby two-dimensionally detecting secondary electrons irradiated from (emitted from) the sample and reading a secondary electron image, wherein a detection sample is formed in a rectangular parallelepiped shape with a width that is almost equal to or smaller than a diameter of the electron beam in a transverse direction of the detection sample, and when the detection sample is placed on the stage and the electron beam irradiates the detection sample and one of that the electron beam is scanned or that the stage is moved is performed, at least one of a scanning direction the electron beam or a movement direction of the stage is corrected so that a light detection time becomes the longest.

When a stage moves in a direction orthogonal to an optical axis or when an electron beam is scanned in a direction orthogonal to the optical axis, the irradiation position of the electron beam on the stage moves in a direction opposite to the stage movement direction or in a direction identical to the electron beam scanning direction. At this time, when the electron beam passes over the detection sample in a rectangular parallelepiped shape, light is irradiated from the surface of the detection sample in the rectangular parallelepiped. A time during which this light is irradiated corresponds to a distance on the detection sample surface in the rectangular parallelepiped on which the electron beam actually moves if the stage movement velocity or the electron beam scanning velocity is constant. Thus, a case where the detection time of light to be detected becomes the longest corresponds to a case in which the electron beam has actually moved along the longitudinal direction of the detection sample in the rectangular parallelepiped.

Therefore, the stage movement direction or electron beam scanning direction when the detection time of light to be detected becomes the longest corresponds to a direction in which the electron beam has actually moved along the longitudinal direction of the detection sample. At least one of the electron beam scanning direction and the stage movement direction is corrected so that the light detection time becomes the longest.

In this manner, the stage movement direction can coincide with the actual electron beam movement direction precisely, thus enabling correction with high precision.

According to a sixth aspect of the present invention, there is provided a scanning electron microscope according to the fifth aspect thereof, wherein, after the stage, in a state in which the movement direction of the electron beam on the detection sample is in a longitudinal direction of the detection sample, is rotated around an optical axis over a predetermined arbitrary angle, and the electron beam irradiates the detection sample and one of that the electron beam is scanned or that the stage is moved is performed, a stage rotation control amount for rotating the stage is corrected so that an angle of intersection, between the one of the scanning direction of the electron beam or the movement direction of the stage in which a light detection time becomes the longest and the one of the scanning direction of the electron beam or the movement direction of the stage in which a light detection time before the stage is rotated around the optical axis over the predetermined arbitrary angle becomes the longest, coincides with the predetermined arbitrary angle.

According to an eleventh aspect of the present invention, there is provided a scanning electron microscope correction method according to the tenth aspect thereof, wherein, after the stage, in a state in which the movement direction of the electron beam on the detection sample is in a longitudinal direction of the detection sample, is rotated around an optical axis over a predetermined arbitrary angle, and the electron beam irradiates the detection sample and one of that the electron beam is scanned or that the stage is moved is performed, a stage rotation control amount for rotating the stage is corrected so that an angle of intersection, between the one of the scanning direction of the electron beam or the movement direction of the stage in which a light detection time becomes the longest and the one of the scanning direction of the electron beam or the movement direction of the stage in which a light detection time before the stage is rotated around the optical axis over the predetermined arbitrary angle becomes the longest, coincides with the predetermined arbitrary angle.

After correction of the stage movement direction has been performed, when the stage is rotated by an predetermined arbitrary angle, thereby detecting a predetermined direction in which a detection time of light to be detected becomes the longest, the predetermined direction is in a direction in which the electron beam actually moves a long the longitudinal direction of the detection sample.

A crossing angle between the detected predetermined direction (longitudinal direction of the detection sample after the stage has been rotated by the predetermined arbitrary angle) and a direction (longitudinal direction of the detection sample) detected before the stage is rotated corresponds to a stage rotation quantity. Thus, the crossing angle ideally coincides with the predetermined arbitrary angle. If the stage rotation control amount is deviated from the actual stage rotation angle, the stage rotation control amount for rotating the stage is corrected so that the crossing angle coincides with the predetermined arbitrary angle. In this manner, the actual stage rotation control amount and the stage rotation angle corresponding to the rotation control amount can be accurately corrected.

According to a seventh aspect of the present invention, there is provided a scanning electron microscope correction method according to the fifth or sixth aspect thereof, wherein at least two detection samples in rectangular parallelepiped shapes are placed on the stage parallel to each other, and when the electron beam irradiates one of the detection samples in rectangular parallelepiped shapes and one of that the electron beam is scanned or that the stage is moved is performed, at least one of the electron beam scanning amount and the stage movement amount is corrected with the one of the scanning direction of the electron beam or the movement direction of the stage, in which the light detection time becomes the longest being defined as a reference direction, and when an electron beam irradiates another of the detection samples in a rectangular parallelepiped shape, and one of that the electron beam is scanned or that the stage is moved is performed, at least one of the electron beam scanning direction and the stage movement direction is corrected so that the one of the scanning direction of the electron beam or the movement direction of the stage when the light detection time becomes the longest coincides with the reference direction.

According to a twelfth aspect of the present invention, there is provided a scanning electron microscope correction method for two-dimensionally scanning an electron beam with respect to a sample, thereby two-dimensionally detecting secondary electrons irradiated from the sample and reading a secondary electron image, wherein at least two detection samples in rectangular parallelepiped shapes are placed on the stage parallel to each other, and when the electron beam irradiates one of the detection samples in rectangular parallelepiped shapes and one of that the electron beam is scanned or that the stage is moved is performed, at least one of the electron beam scanning amount and the stage movement amount is corrected with one of the scanning direction of the electron beam or the movement direction of the stage, in which the light detection time becomes the longest being defined as a reference direction, and when an electron beam irradiates another of the detection samples in a rectangular parallelepiped shape, and one of that the electron beam is scanned or that the stage is moved is performed, at least one of the electron beam scanning direction and the stage movement direction is corrected so that the one of the scanning direction of the electron beam or the movement direction of the stage when the light detection time becomes the longest coincides with the reference direction.

At least two detection samples in rectangular parallelepipeds shape are placed on a stage in parallel to each other. After correction in the stage movement direction has been performed by employing one of these detection samples in rectangular parallelepipeds, when there is detected a direction (one of the scanning direction of the electron beam or the movement direction of the stage) in which the detection time of light becomes the longest in another detection sample in a rectangular parallelepiped shape, the direction is in a direction in which the electron beam actually moves along the longitudinal direction of the other detection sample.

The detected direction ideally coincides with a longitudinal direction of the one detection sample in a rectangular parallelepiped when correction in the stage movement direction is performed by employing the one detection sample in a rectangular parallelepiped. However, if the parallelism of beam scanning is shifted or if an error occurs with the parallelism in the stage movement direction, such coincidence is not obtained.

Because of this, at least one of the electron beam scanning direction and the stage movement direction is corrected so that the detected direction coincides with the longitudinal direction of the one detection sample in a rectangular parallelepiped when correction in the stage movement direction is performed by employing the one detection sample in a rectangular parallelepiped. In this manner, the precision in parallelism of electron beam scanning can be corrected with high precision.

According to an eighth aspect of the present invention, there is provided in a scanning electron microscope correction method according to anyone of the first to seventh aspects thereof, wherein the detection sample is formed of a material that generates light of a single wavelength by being the electron beam irradiated, the detection sample being formed in a substantially rectangular parallelepiped shape with a width that is almost equal to or smaller than a diameter of the electron beam in a transverse direction of the detection sample, one side face of two side faces of the detection sample being a reflection surface for reflecting the light of the single wavelength, the light that transmits within the detection sample and reaches the other side surface is detected at the other side surface, an actual irradiation position of the electron beam is detected based on the detected light intensity, and a scanning control amount of the electron beam is corrected so that a designated electron beam irradiation position coincides with the actual electron beam irradiation position.

According to a thirteenth aspect of the present invention, there is provided a scanning electron microscope correction method for two-dimensionally scanning an electron beam with respect to a sample, thereby two-dimensionally detecting secondary electrons irradiated from the sample and reading a secondary electron image, wherein a detection sample is formed of a material that generates light of a single wavelength by being the electron beam irradiated, the detection sample being formed in a substantially rectangular parallelepiped shape with a width that is almost equal to or smaller than a diameter of the electron beam in a transverse direction of the detection sample, one side face of two side faces of the detection sample being a reflection surface for reflecting the light of the single wavelength, the light that transmits within the detection sample and reaches the other side surface is detected at the other side surface, an actual irradiation position of the electron beam is detected based on the detected light intensity, and a scanning control amount of the electron beam is corrected so that a designated electron beam irradiation position coincides with the actual electron beam irradiation position.

Light is irradiated from the irradiation position of an electron beam on a detection sample, and the irradiated light propagates (transmits) the inside of the detection sample. According to the present invention, there is employed a columnar detection sample that comprises a reflection surface, for reflecting the light with its single wavelength, which is one of side surfaces opposing each other, wherein a part of the light generated from an electron beam irradiation position (referred to as a first light) propagates the inside of the detection sample, and reaches the reflection surface, and is reflected on the reflection surface to go to another side surface opposite to the reflection surface.

In addition, another part of the light generated from the electron beam irradiation position (referred to as a second light) goes to the side surface opposite to the reflection surface. Thus, the light going to the side surface opposite to the reflection surface from the electron beam irradiation position becomes interference light due to the first light and the second light.

Here, a relative phase angle of the first light is equal to that of the second light, the first and second lights are mutually emphasized, and an amplitude is a maximum. If the relative phase angles are 180 degrees, these light are offset, and the amplitude is minimal, i.e., 0. A factor of determining this relative phase difference lies in an optical path length (distance) D from a light generation point (i.e., light irradiation position) to the reflection surface. Assuming that the wavelength is $\lambda$, when $D=((\lambda/2)\times(2n))$ (provided if 'n' denotes a natural number), the relative phase angles of the first and second lights is set to 0 degree, and the first and second lights are mutually emphasized. When $D=((\lambda/2)\times(2n+1))$, the relative phase angles of the first and second lights is set to 180 degrees, and the first and second lights are offset. By virtue of the above reason, the intensity of the light going to the side surface opposite to the reflection surface periodically changes gradually from the maximum intensity to the minimum intensity.

Therefore, the actual irradiation position (movement amount) of the electron beam can be accurately detected based on a relationship between an electron beam scanning distance and the detected light intensity.

In this manner, there can be detected the quantity of displacement between the actual irradiation position (movement amount) of the detected electron beam and an irradiation position of the electron beam caused by scanning, and the electron beam irradiation position caused by scanning can be corrected with high precision according to the displacement quantity.

BRIEF DESCRIPTION OF THE DRAWINGS

FIG. 1 is an explanatory view illustrating a schematic structure of a scanning electron microscope according to an embodiment of the present invention.

DETAILED DESCRIPTION OF PREFERRED EMBODIMENTS

Figure 2:
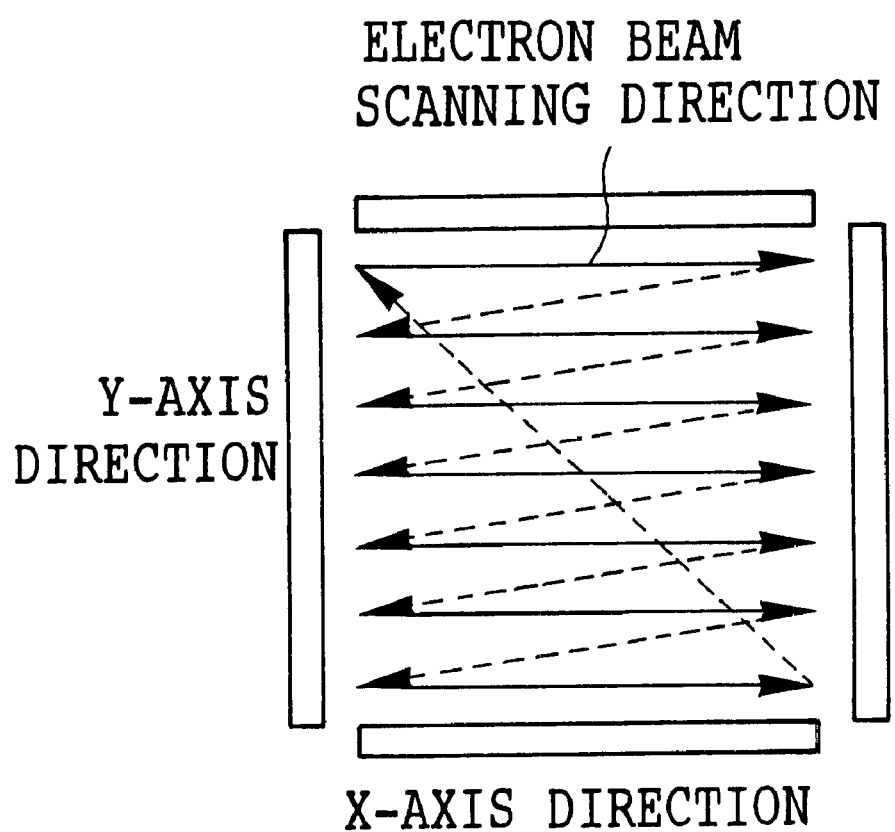
FIG. 2 is an explanatory view illustrating an example of a scanning direction of an electron beam of the scanning electron microscope shown in FIG. 1.

In FIG. 1, there is schematically shown a structure of a scanning electron microscope (hereinafter, referred to as an SEM) according to an embodiment of the present invention. As shown in FIG. 1, the SEM according to the illustrative embodiment has an electron gun 10 for generating an electron, an electromagnetic lenses (an electromagnetic lens group) 12, a beam-scanning electrode 14, an electromagnetic lens 16 for controlling a focal position, a secondary electron detecting section 18, a visible light detector 20, a stage 22, a stage driving section 24, a display 26, and a controller 28.

The electromagnetic lenses 12 converges an electron beam from the electron gun 10 so that the electron beam is guided to the stage 22. The beam-scanning electrode 14 provided at the rear step of the electromagnetic lenses 12 controls a state in which a magnetic field is produced, thereby controlling an irradiation position on the stage 22, of an electron beam converged by the electromagnetic lenses 12.

The electromagnetic lens 16 for controlling a focal position provided at the rear step of the beam-scanning electrode 14 controls the intensity of a magnetic field, thereby adjusting a focal position of an electron beam when the irradiation position of the electron beam is controlled by the beam-scanning electrode 14. In general, as shown in FIG. 2, an electron beam is scanned in an X-axis direction from a start point to an end point, then, is moved from the end point in the X-axis direction to the next start point that is slightly shifted from the start point in a Y-axis direction, and is scanned again in the X-axis direction.

The secondary electron detecting section 18 complements each secondary electron generated from the sample surface when an electron beam irradiates the detection sample placed on the stage 22. Then, the secondary electron is converted into the corresponding electrical signal by means of a fluorescent screen or the like. Then, the converted signal is amplified by means of a photoelectric multiplier such as photo-multiplier, and the amplified signal is outputted to the display 26.

The visible light detector 20 detects light irradiated from the sample surface when an electron beam irradiates the detection sample placed on the stage 22. The detected light (results of the light detection) is then outputted to the controller 28.

The stage 22 is provided with a mounting surface 22a on which a sample is mounted. The mounting surface 22a is arranged movably in an X-axis direction, a Y-axis direction orthogonal to the X-axis direction, and a Z-axis direction orthogonal to an XY plane. The movement of the stage 22 is controlled by the stage driving section 24 that is driven based on an instruction from the controller 28.

The display section 26 is composed of a CRT and the like, and displays an image based on an electrical signal from the secondary detecting section 18 as a sample image (SEM image) The display section 26 can be configured so as to display a text image based on data outputted from the controller 28.

In addition, the controller 28 controls the electron gun 10, the electromagnetic lenses 12, the electromagnetic lens 16 for controlling a focal position, the beam-scanning electrode 14, and the stage driving section 24, respectively. The controller performs SEM correction processing based on a correction program.

Figure 3:
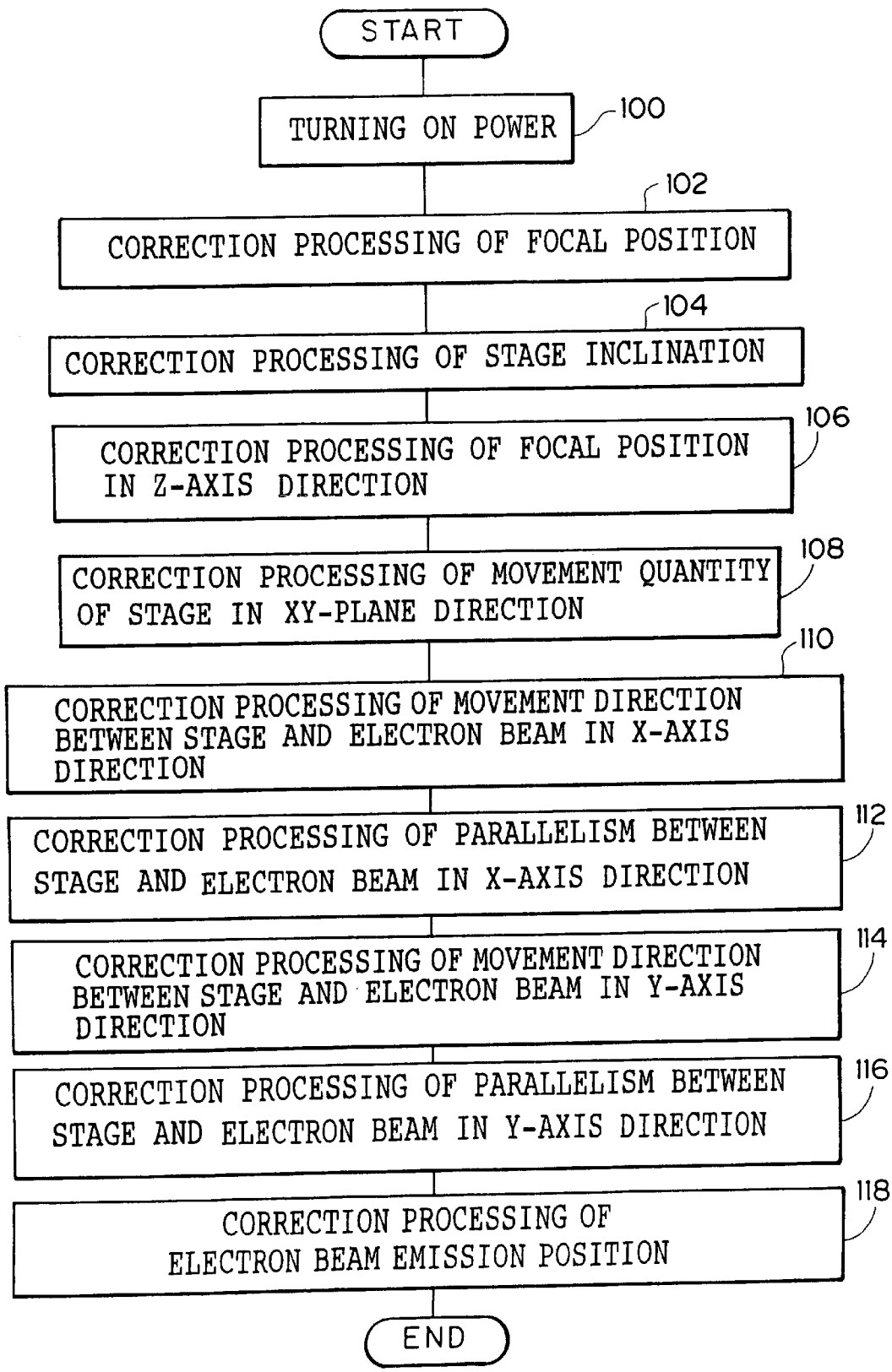
FIG. 3 is a flow chart illustrating a flow of SEM correction processing based on a correction program of the scanning electron microscope shown in FIG. 1.

Now, SEM correction processing based on a correction program using the controller 28 will be described with reference to the flow chart shown in FIG. 3. At the step 100 shown in FIG. 3, the SEM is powered on, and, when, a wafer-shaped (substantially circular) correction sample 30 is placed on the mounting surface 22a of the stage 22, the current step goes to step 102, at which correction processing of a focal position of an electron beam is started. A wafer-shaped correction sample 30, for example, of 10 mm in diameter and 100.nm in thickness is placed on the mounting surface 22a. This correction sample 30 is composed of a material that is excited by the irradiation of an electron beam (by being irradiated by an electron beam) to generate an electromagnetic wave in a visible light beam region. The surface is smooth, and a very thin carbon is vapor deposited, whereby continuity is ensured.

In correction processing of the focal position of an electron beam, the position of the stage is first fixed at a reference position (point 0) by the stage driving portion 24, and an electron beam is produced from the electron gun 10. Then, the electromagnetic lenses 12, the electromagnetic lens 16 for controlling a focal position, and the beam-scanning electrode 14 are controlled so that an electron beam irradiates one point of the correction sample 30 on the mounting surface 22a. When the electron beam irradiates one point of the correction sample 30 on the mounting surface 22a, the settings of the electromagnetic lenses 12, the electromagnetic lens 16 for controlling a focal point, and the beam-scanning electrode 14 are fixed.

Figure 4:
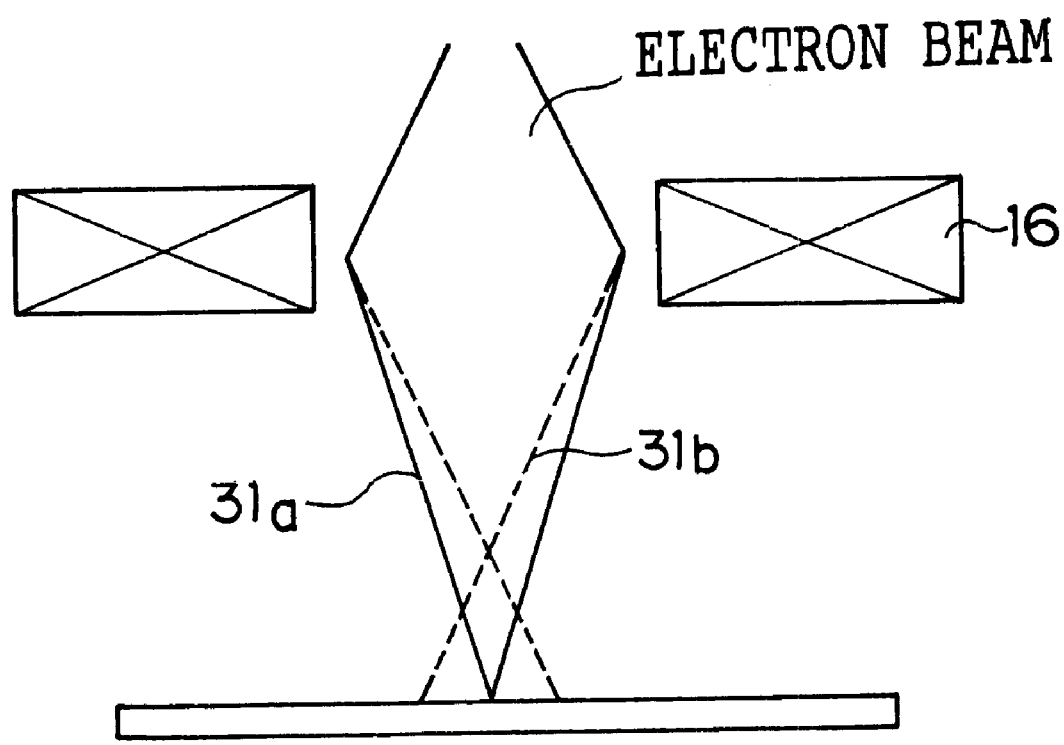
FIG. 4 is an explanatory view illustrating a states in which electron beam is in focus and out of focus.

In a case where the electron beam is in focus (in the case where a focal point is on the surface of the correction sample 30), as shown in a line 31a of FIG. 4, the electron beam gathers on one point on the surface of the correction sample 30, and the electron density is a maximum. Otherwise, as shown in a dotted line 31b of FIG. 4, in which the electron beam is out of focus, the electron beam gathers on one point other than the surface of the correction sample 30. As a result, the electron beam irradiates a circular region, not one point, on the surface of the correction sample 30. Thus, the electron density is smaller than when the electron beam gathers on one point on the surface of the correction sample 30.

The correction sample 30 generates light that has an intensity corresponding to the electron density of the electron beam. When the electron beam is in focus, light of a maximum intensity is detected by the visible light detector 20. If the electron beam is out of focus, the light of an intensity smaller than the light with the maximum intensity is detected.

The controller 28 sets to a reference control amount the control amount of the electromagnetic lens 16 for controlling a focal position (e.g., current value or voltage value and the like applied to the electromagnetic lens 16 for controlling a focal position; the same hereinafter). Thereafter, the controller 28 varies the control amount of the electromagnetic lens 16 for controlling a focal position within a predetermined range whose center is the reference control amount described above. At this time, the controller 28 surveils (monitors) light intensity by the visible light detector 20, and judges whether or not the control amount when the light intensity is at a maximum coincides with the reference control amount.

In a case where it has been judged that the control amount of the electromagnetic lens 16 for controlling a focal position when the light of a maximum intensity is detected coincides with the reference control amount of the electromagnetic lens 16 for controlling a focal position, an electrically controlled focal position coincides with an actual focal position of an electron beam (when the reference control amount is applied to the electromagnetic lens 16 for controlling a focal position, the focal point of the electron beam is defined on the surface of the correction sample 30). Then, the current step goes to the next step 104.

Alternatively, in a case where it has been judged that the control amount of the electromagnetic lens 16 for controlling a focal position when the light with its maximum intensity is detected does not coincide with the reference control amount of the electromagnetic lens 16 for controlling a focal position, an electrically controlled focal position does not coincide with the actual focal position of the electron beam. Thus, the reference control amount of the electromagnetic lens 16 for controlling a focal position is corrected to the control amount when the light of a maximum intensity is detected. Then, the current step goes to the next step 104. In this manner, the electrically controlled focal position coincides with the actual focal position of the electron beam, and thus, the SEM image on the actual sample surface can be accurately displayed.

At the next step 104, correction processing of an inclination of the stage 22 is performed. First, the controller 28 moves the stage 22 by means of the stage driving section 24 in the XY direction only by a predetermined distance, and fixes the position of the stage 22.

Next, the controller 28 produces an electron beam from the electron gun 10 (The controller 28 instructs that an electron beam is irradiated from (emitted by) the electron gun 10). While the light intensity from the sample 30 is surveilled by the visible light detector 20, the control amount of the electromagnetic lens 16 for controlling a focal position is varied within the predetermined range whose center is the control amount of the focal position corrected at the step 102. Then, it is judged whether or not the control amount when the light intensity is a maximum coincides with the control amount of the focal position corrected at the step 102.

In a case in which the control amount when the light intensity is a maximum coincides with the control amount of the focal position corrected at the step 102, the stage 22 is not inclined. Thus, the current step goes to the next step 106. When the control amount when the light intensity is a maximum does not coincide with the control amount of the focal position corrected at the step 102, the stage 22 is inclined. Accordingly, the inclination of the stage 22 is corrected by the stage driving section 24 so that the control amount when the light intensity is a maximum coincides with the control amount of the focal position corrected at the step 102, and the current step goes to step 106.

At the next step 106, vertical direction correction processing of the stage 22 is performed. First, the controller 28 moves the stage 22 in a Z-axis direction only by a predetermined distance by the stage driving section 24, and fixes the position of the stage 22.

Next, the controller 28 produces an electron beam from the electron gun 10, and moves the focal position of the electron beam in the Z-axis direction by means of the electromagnetic lens 16 for controlling a focal position. At this time, the adjustment amount of the electromagnetic lens 16 for controlling a focal position is set so that the focal position of the electron beam is shifted in the Z-axis direction only by said predetermined distance. Then, the control amount of the electromagnetic lens 16 for controlling a focal position is varied within the predetermined range whose center is this adjustment amount.

The controller 28 surveils the light intensity of the sample by the visible light detector 20, and judges whether or not the adjustment amount when the light intensity is a maximum coincides with the control amount preset for the electromagnetic lens 16 for controlling a focal position in which focal position is shifted in the Z-axis direction only by said predetermined distance.

When the adjustment amount when the light intensity is a maximum coincides with the control amount preset for the electromagnetic lens 16 for controlling a focal position in which the focal position is shifted in the Z-axis direction only by said predetermined distance, the movement amount of the stage 22 in the Z-axis direction caused by the stage driving section 24 matches the movement amount of the focal position caused by the electromagnetic lens 16 for controlling a focal position. The current step goes to the next step 108.

When the adjustment amount when the light intensity is a maximum does not coincide with the control amount preset for the electromagnetic lens 16 for controlling a focal position in which the focal position is shifted in the Z-axis direction only by said predetermined distance, the focal position of the electron beam is not on the surface of the correction sample 30 on the mounting surface 22*a*. Namely, the movement amount of the stage 22 in the Z-axis direction caused by the stage driving section 24 does not match the movement amount in the Z-axis direction of the focal position caused by the electromagnetic lens 16 for controlling a focal position. Thus, there is detected a correlation between the movement amount (said predetermined distance) of the stage 22 in the Z-axis direction caused by the stage driving section 24 and the adjustment amount of the focal position caused by the electromagnetic lens 16 for controlling a focal position when the light detected by the visible light detector 20 is a maximum. Based on this correlation, the adjustment amount of the focal position caused by the electromagnetic lens 16 for controlling a focal position is corrected. Then, the current step goes to the next step 108.

In this manner, the movement amount in the Z-axis direction caused by electrical control coincides with the actual movement amount of the focal position of the electron beam in the Z-axis direction by the stage driving section 24, and thus, the actual SEM image on the sample surface can be accurately displayed.

At the step 108, correction processing of the horizontal movement amount of the stage 22 is performed. First, there is provided a plurality of cube-shaped correction samples 30 of 500 nm in length of one side, for example. These samples are placed on the mounting surface 22*a*, and a mutual distance between the correction samples 30 is strictly measured. This correction sample 30 is composed of a material that is excited by an electron beam irradiation to generate an electromagnetic wave in a visible light beam region. The surface is smooth, and a very thin carbon is vapor deposited, whereby the electric continuity is ensured.

Next, the controller 28 fixes the position of the stage 22 to a reference position (point 0) by means of the stage driving section 24, and fixes settings of the electromagnetic lenses 12, the electromagnetic lens 16 for controlling a focal position, and the beam-scanning electrode 14.

Thereafter, the controller 28 produces an electron beam from the electron gun 10. The stage 22 is moved in a predetermined direction in the XY plane by means of the stage driving section 24, thereby controlling the electron beam so that the electron beam passes over at least two correction samples 30.

At this time, the controller 28 surveils the movement amount of the stage 22 according to electrical control amount caused by the stage driving section 24 and a timing of detecting the light by the visible light detector 20. Then, the controller computes the actual movement amount of the movement of electron beam on the basis of the light detection timing and the movement velocity of the stage 22, and judges whether or not the computed movement amount coincides with that of the stage 22 according to the electrical control caused by the stage driving section 24.

When the actual (computed) movement amount coincides with that of the stage 22 according to the electrical control caused by the stage driving section 24, the movement amount in a predetermined direction in the XY plane of the stage 22 according to the electrical control caused by the stage driving section 24 coincides with actual electron beam movement amount. Then, the current step goes to the next step 110.

When the actual movement amount does not coincide with that of the stage 22 according to the electrical control amount caused by the stage driving section 24, the movement amount in a predetermined direction in XY plane of the stage 22 according to the electrical control amount caused by the stage 24 is deviated from the actual movement amount in a predetermined direction in the XY plane of the electron beam. Thus, the electrical control caused by the stage driving section 24 is corrected so that the movement amount in a predetermined direction in the XY plane of the stage 22 according to the electrical control amount caused by the stage driving section 24 coincides with the actual movement amount in the predetermined direction in the XY plane of the electron beam. Then, the current step goes to the step 110.

At the step 110, there is performed correction processing of the movement direction of the stage 22 in the X-axis direction and the scanning direction of the electron beam in the X-axis direction caused by the beam-scanning electrode 14. First, for example, there is provided one rod shaped correction sample 30 of 100 mm in longitudinal length, 500 nm in transverse length, and 500 nm in thickness. This sample is disposed at the center of the mounting surface 22*a* so that the movement direction in the X-axis direction caused by the stage driving section 24 and longitudinal direction of this sample strictly coincide with each other. This correction sample 30 is also composed of a material that is excited by being electron beam irradiated to generate an electromagnetic wave in the visible light beam region. The surface is smooth, and a very thin carbon is vapor deposited, whereby the electric continuity is ensured.

Next, in the controller 28 controls such that an electron beam is scanned on the correction sample 30 in the X-axis direction by means of the beam-scanning electrode 14, after one scan has completed, the stage 22 is rotated by a predetermined angle by means of the stage driving section 24, then, an operation for scanning an electron beam in the X direction by means of the beam-scanning electrode 14 is done, and the above operation is repeated.

At this time, the controller 28 surveils the detection time of the light from the visible light detector 20, and detects a rotation angle of the stage 22 when the detection time of the light being the longest is detected. If the detected rotation angle is 0 degrees, the movement direction in the X direction caused by the stage driving section 24 coincides with the movement direction of the electron beam in the X direction caused by the beam-scanning electrode 14. Then, the current step goes to the step 112.

Alternatively, if a detected rotation angle in the stage 22 corresponding to the detection time of the light being the longest is a rotation angle other than 0 degrees, the movement direction of the electron beam in the X direction is rotated by the rotation angle. Then, correction is performed so that the movement direction in the X-axis direction caused by the stage driving section 24 coincides with the movement direction of the electron beam in the X-axis direction caused by the beam-scanning electrode 14. Then, the current step goes to the step 112.

At the step 112, there is performed correction processing of the parallelism in the movement direction of the stage 22 in the X direction. Correction samples 30 having shapes the same as those employed at the step 110 are employed. These samples are plurally disposed parallel to one another at intervals of 5 mm, for example, so that the movement direction in the X direction caused by the stage driving section 24 and longitudinal direction of these samples strictly coincide with each other.

The processing of each of correction samples 30 is similar to the step 110, and thus, a description will be omitted here. At the step 112, rotation angles are detected by the number of correction samples 30 placed on the placement surface, and thus, it is judged as to whether all the rotation angles coincide with each other.

In a case in which all the rotation angles coincide, the current step goes to the step 114. When all the rotation angles do not coincide, the adjustment amount of the scanning direction of the electron beam in the X direction caused by the beam-scanning electrode 14 is corrected so that all the rotation angle coincide with each other.

At the step 114, there is performed correction processing of the movement direction of the stage 22 in the Y-axis direction and the electron beam in the Y-axis direction caused by the beam-scanning electrode 14. After the stage 22 is rotated by 90 degrees, subsequent processing similar to the aforementioned step 110 is performed, and thus, a description will be omitted here.

At the step 116, there is performed correction processing of the parallelism of the movement direction of the stage 22 in the Y-axis direction. Correction samples 30 having shapes the same as those employed at the step 112 are employed, and the stage 22 is rotated by 90 degrees. The subsequent processing similar to the aforementioned step 110 is performed, and thus, a description will be omitted here.

Figure 5:
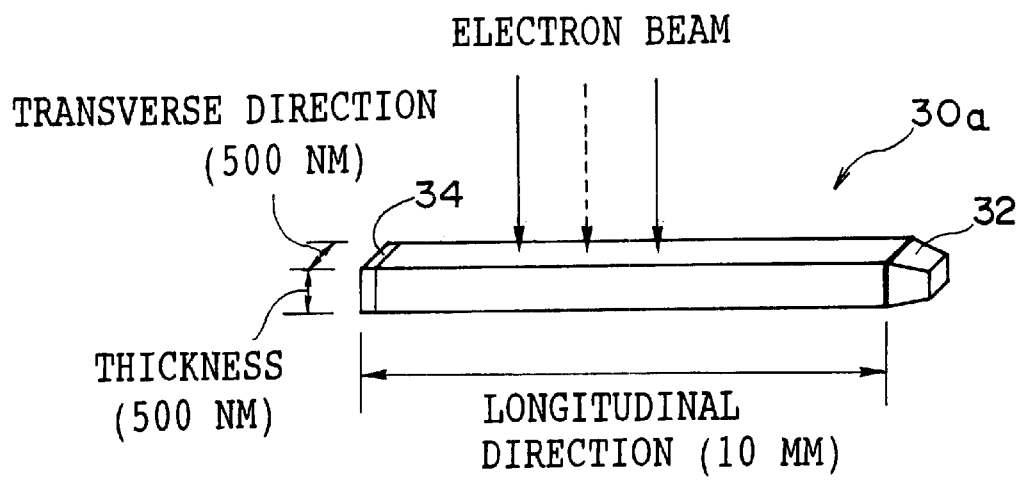
FIG. 5 is an explanatory view illustrating an example of a configuration for a correction sample used for correction processing of an irradiation position of an electron beam.
Figure 6:
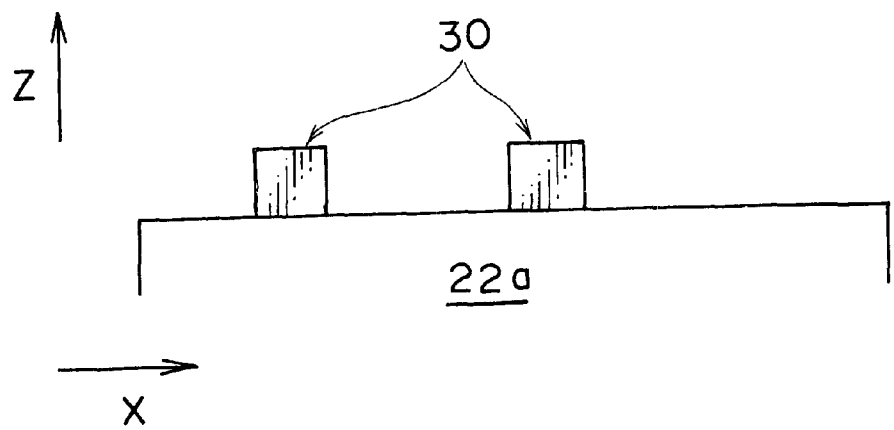
FIG. 6 is an explanatory view illustrating a states in which a plurality of detection samples (cubic shape) are placed on the stage.
Figure 7:
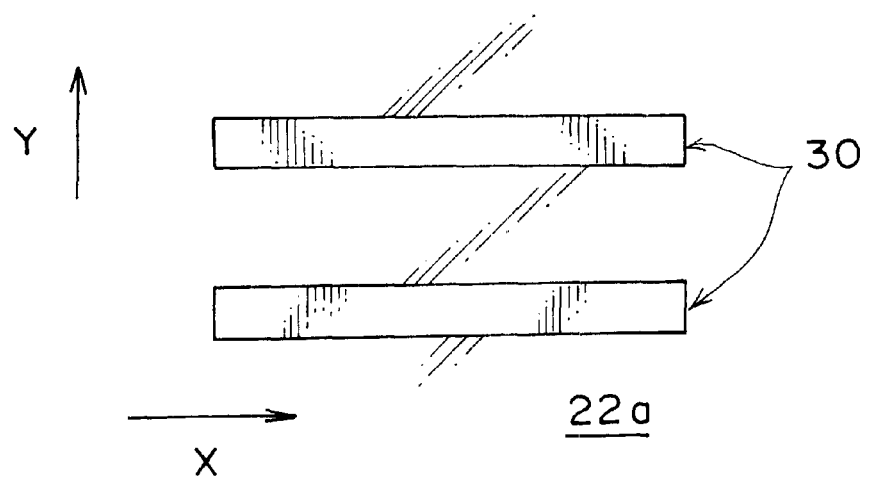
FIG. 7 is an explanatory view illustrating a state in which a plurality of detection samples (rectangular parallelepiped shape) is placed on the stage.

At the step 118, correction processing of the movement amount of an electron beam irradiation position is performed. On the mounting surface 22*a*, there is placed a correction sample 30*a* formed in a columnar shape of 10 mm in longitudinal length, 500 nm in transverse length, and 500 nm in thickness, for example, as shown in FIG. 5, the sample being provided on a molybdenum or tungsten substrate.

This correction sample 30*a* is composed of a material that produces an electromagnetic wave of a designated wavelength, in particular light in the visible light region, by being irradiated by an electron beam. For example, YAG:Nd ($Nd^{3+}$720 nm to 830 nm) obtained by substituting part of $Y^{3+}$ of $Y_3Al_5O_{12}$ by $Nd^{3+}$ may structure the material.

In addition, an Al film 34 is formed on one side surface in the longitudinal direction of the correction sample 30*a* by means of vapor deposition. This Al film 34 reflects light that transmits in the inside of the correction sample 30*a*. A detector 32 is formed on the side surface opposite to the one side surface (reflection surface). This detector 32 is composed of an infrared-ray detector such as PbSe or PbS, for example. The intensity of the light transmitted in the inside of the correction sample 30*a* and reaching the detector 32 is detected, and is outputted to the controller 28.

The surface on which the electron beam of the correction sample 30*a* is irradiated is smooth, and a very thin carbon film is vapor deposited, whereby the electric continuity is ensured. This correction sample 30*a* is disposed on the mounting surface 22*a* so that the longitudinal direction coincides with one of the X and Y-axis directions.

The controller 28 fixes the position of the stage 22 to a reference position (point 0) by means of the stage driving section 24, and instructs that an electron beam is produced from the electron gun 10. Then, the controller controls the electromagnetic lenses 12, electromagnetic lens 16 for controlling a focal position, and beam-scanning electrode 14 so that the electron beam irradiates one point of the correction sample 30*a* on the mounting surface 22*a*.

Next, the beam-scanning electrode 14 is controlled, whereby the electron beam irradiation position is moved by means of the beam-scanning electrode 14 so that the irradiation position of the electron beam on the correction sample 30*a* moves along the longitudinal direction of the correction sample 30*a* with a predetermined interval distance (for example, 2 μm)

At this time, an electromagnetic wave in a visible light region of 532 nm in wavelength is generated from the electron beam irradiation position, and is transmitted in the inside of the columnar correction sample 30*a*. Of these electromagnetic waves, the electromagnetic wave that is transmitted toward the Al film 34 along the longitudinal direction is reflected by means of the Al film 34, and is transmitted toward the detector 32. Then, the electromagnetic wave reflected by the Al film 34 is detected by means of the detector 32 together with the electromagnetic wave that has been transmitted toward the detector 32.

At this time, the electron beam irradiation position is moved, whereby the reciprocating optical path length varies, and thus, the movement of the electron beam irradiation position has an effect twice as much as usual. Therefore, a distance between an electron beam irradiation position at which the light intensity is a maximum due to an enhancement effect caused by interference and an electron beam irradiation position at which the light intensity is a minimum due to an offset effect caused by interference is half of the wavelength, 0.266 microns, for example.

The controller 28 records the intensity of light irradiation from the detector 32 mounted on a surface opposite to the reflection surface of the correction sample 30*a* and a control signal for the beam-scanning electrode 14 required for movement of electron beams.

The intensity of light irradiation from the detector 32 increases and decreases periodically due to an interference effect. Thus, an actual accurate movement amount (movement amount of electron beam on the sample quantity surface) of electron beam can be detected by this periodic increase and decrease and by the control signal for the beam-scanning electrode 14.

In this manner, there is obtained a correlation with the control signal for the beam-scanning electrode 14 required for movement of electron beams based on the actual accurate movement amount of the detected electron beams. Then, the movement amount of the electron beam controlled by means of the control signal for the beam-scanning electrode 14 can coincide with the actual movement amount of the electron beam with high precision, based on the correlation. After correction processing of the movement amount (irradiation position) of such electron beam has terminated, SEM correction processing based on the correction program terminates. Thus, this routine is terminated.

In this way, in the present embodiment, as SEM correction processing based on the correction program, there are sequentially performed correction processing of a focal position, correction processing of inclination of the stage 22, correction processing of the movement amount of the focal position in a Z-axis direction, correction processing of the movement amount of the stage 22 in the XY-plane direction, correction processing of the movement direction in the X direction between the stage 22 and the electron beam, correction processing of the parallelism in the X direction between the stage 22 and the electron beam, correction processing of the movement direction in the Y-axis direction between the stage 22 and the electron beam, correction processing of the parallelism in the Y-axis direction between the stage 22 and the electron beam, and correction processing of the electron beam movement amount (irradiation position), thereby enabling correction with high precision such that the user-defined electron beam irradiation position accurately coincides with an actual electron beam irradiation position.

In the present embodiment, as SEM correction processing based on the correction program, there are sequentially performed correction processing of a focal position, inclination correction processing of the stage 22, correction processing of the movement amount of the focal position in a Z-axis direction, correction processing of the movement amount of the stage 22 in the XY-plane direction, correction processing of the movement direction in the X direction between the stage 22 and the electron beam, correction processing of the parallelism in the X direction between the stage 22 and the electron beam, correction processing of the movement direction in the Y-axis direction between the stage 22 and the electron beam, correction processing of the parallelism in the Y-axis direction between the stage 22 and the electron beam, and correction processing of the electron beam movement amount (irradiation position). The sequence of the above correction processes after the correction processing of the focal position is not limited to the above.

In SEM correction processing based on the correction program, after correction processing of the focal position has been performed, there may be performed at least one of inclination correction processing of the stage 22, correction processing of the movement amount of the focal position in a Z-axis direction, correction processing of the movement amount of the stage 22 in the XY-plane direction, correction processing of the movement direction in the X direction between the stage 22 and the electron beam, correction processing of the parallelism in the X direction between the stage 22 and the electron beam, correction processing of the movement direction in the Y-axis direction between the stage 22 and the electron beam, correction processing of the parallelism in the Y-axis direction between the stage 22 and the electron beam, and correction processing of the electron beam movement amount (irradiation position). The present invention is not limited to numeric values described in the present embodiment.

In the present embodiment, although SEM correction processing is automatically performed based on the correction program incorporated in the controller 28, it is possible to perform correction processing manually while the user makes a visual check.

As has been described above, according to the present invention, there is provided an advantageous effect that a user-defined electron beam irradiation position accurately coincides with an actual electron beam irradiation position, enabling correction with high precision.

What is claimed is:

1. A scanning electron microscope correction method comprising the steps of:

setting a detection sample on a movable stage of the scanning electron microscope for producing light of an intensity corresponding to an electron density of an electron beam irradiating a surface of the detection sample;

irradiating with the electron beam a predetermined position of the detection sample placed on the movable stage of the scanning electron microscope;

detecting the intensity of the light produced from the detection sample; and performing correction relating to the scanning electron microscope on the basis of the intensity of the detected light.

2. A scanning electron microscope correction method according to claim 1, wherein one of a movement control amount of a focal position of the electron beam in an optical axis direction and a movement control amount of the stage in the optical axis direction is corrected at a plurality of positions on the stage.

3. A scanning electron microscope correction method according to claim 2, wherein the movement control amount of the stage in the optical axis direction and the movement control amount of the focal position of the electron beam in the optical axis direction are corrected on the basis of a correlation between a predetermined movement amount of the stage in the optical axis direction, and a movement amount of the focal position of the electron beam in the optical axis direction when the focal position of the electron beam is moved in the optical axis direction so that the light intensity is a maximum after the stage, in a state in which the focal position of the electron beam is set on the detection sample, has been moved in the optical axis direction by the predetermined movement amount.

4. A scanning electron microscope correction method according to claim 1, wherein a plurality of detection samples are disposed on the stage at known intervals, and a movement control amount of the stage with respect to an actual movement amount of the stage is corrected on the basis of the movement control amount of the stage from a position at which the electron beam irradiates a first detection sample which is one of the plurality of detection samples to a position at which the electron beam irradiates a second detection sample which is another of the plurality of detection samples, at a time the stage is moved linearly such that the electron beam irradiates the first detection sample and the second detection sample, and on the basis of a distance between the first detection sample and the second detection sample.

5. A scanning electron microscope correction method according to claim 1, wherein the detection sample is formed in a rectangular parallelepiped shape with a width that is almost equal to or smaller than a diameter of the electron beam in a transverse direction of the detection sample, and wherein, when the detection sample is placed on the stage and the electron beam irradiates the detection sample and one of that the electron beam scans or that the stage is moved is performed, at least one of a scanning direction of the electron beam or a movement direction of the stage is corrected so that a light detection time becomes the longest.

6. A scanning electron microscope correction method according to claim 5, wherein, after the stage, in a state in which the movement direction of the electron beam on the detection sample is in a longitudinal direction of the detection sample, is rotated around an optical axis over a predetermined arbitrary angle, and the electron beam irradiates the detection sample and one of that the electron beam scans or that the stage is moved is performed, a stage rotation control amount for rotating the stage is corrected so that an angle of intersection, between the one of the scanning direction of the electron beam or the movement direction of the stage in which a light detection time becomes the longest and the one of the scanning direction of the electron beam or the movement direction of the stage in which a light detection time before the stage is rotated around the optical axis over the predetermined arbitrary angle becomes the longest, coincides with the predetermined arbitrary angle.

7. A scanning electron microscope correction method according to claim 5, wherein at least two detection samples in rectangular parallelepiped shapes are placed on the stage parallel to each other, and wherein, when the electron beam irradiates one of the detection samples in rectangular parallelepiped shapes and one of that the electron beam scans or that the stage is moved is performed, at least one of the electron beam scanning amount and the stage movement amount is corrected with the one of the scanning direction of the electron beam or the movement direction of the stage, in which the light detection time becomes the longest being defined as a reference direction, and wherein, when an electron beam irradiates another of the detection samples in a rectangular parallelepiped shape, and one of that the electron beam scans or that the stage is moved is performed, at least one of the electron beam scanning direction and the stage movement direction is corrected so that the one of the scanning direction of the electron beam or the movement direction of the stage when the light detection time becomes the longest coincides with the reference direction.

8. A scanning electron microscope correction method according to claim 1, wherein the detection sample is formed of a material that generates light of a single wavelength by being irradiated by the electron beam, the detection sample being formed in a substantially rectangular parallelepiped shape with a width that is almost equal to or smaller than a diameter of the electron beam in a transverse direction of the detection sample, one side face of two side faces of the detection sample being a reflection surface for reflecting the light of the single wavelength, the light that propagates within the detection sample and reaches the other side surface is detected at the other side surface, an actual irradiation position of the electron beam is detected based on the detected light intensity, and a scanning control amount of the electron beam is corrected so that a designated electron beam irradiation position coincides with the actual electron beam irradiation position.

9. A scanning electron microscope correction method for two-dimensionally scanning a sample with an electron beam, and two-dimensionally detecting secondary electrons irradiated from the sample and reading a secondary electron image, said method employing a plurality of respective detection samples, each respective detection sample generating light of a predetermined intensity corresponding to an electron density of the electron beam irradiating a surface of the respective detection sample, wherein the plurality of detection samples are disposed on the stage at known intervals, and wherein a stage movement control amount with respect to an actual stage movement amount is corrected on the basis of a stage movement control amount from a position at which the electron beam irradiates a first detection sample, which is one of the plurality of detection samples, to a position at which the electron beam irradiates a second detection sample, which is another of the plurality of detection samples, at a time the stage is moved linearly such that the electron beam irradiates the first detection sample and the second detection sample, and on the basis of a distance between the first detection sample and the second detection sample.

10. A scanning electron microscope correction method for two-dimensionally scanning a sample with an electron beam, and two-dimensionally detecting secondary electrons irradiated from the sample and reading a secondary electron image, wherein a detection sample is formed in a rectangular parallelepiped shape with a width that is almost equal to or smaller than a diameter of the electron beam in a transverse direction of the detection sample, the detection sample generating light of a predetermined intensity corresponding to an electron density of the electron beam, as the electron beam irradiates a surface of the detection sample, and when the detection sample is placed on the stage and the electron beam is irradiating the detection sample and one of that the electron beam scans or that the stage is moved is performed, at least one of a scanning direction of the electron beam or a movement direction of the stage is corrected so that a light detection time becomes the longest.

11. A scanning electron microscope correction method according to claim 10, wherein, after the stage, in a state in which the movement direction of the electron beam on the detection sample is in a longitudinal direction of the detection sample, is rotated around an optical axis over a predetermined arbitrary angle, and the electron beam irradiates the detection sample and one of that the electron beam scans or that the stage is moved is performed, a stage rotation control amount for rotating the stage is corrected so that an angle of intersection, between the one of the scanning direction of the electron beam or the movement direction of the stage in which a light detection time becomes the longest and the one of the scanning direction of the electron beam or the movement direction of the stage in which a light detection time before the stage is rotated around the optical axis over the predetermined arbitrary angle becomes the longest, coincides with the predetermined arbitrary angle.

12. A scanning electron microscope correction method for two-dimensionally scanning a sample with an electron beam, and two-dimensionally detecting a secondary electrons irradiated from the sample and reading a secondary electron image, wherein at least two respective detection samples of rectangular parallelepiped shapes are placed on the stage parallel to each other, each respective detection sample generating light of a predetermined intensity corresponding to an electron density of the electron beam irradiated onto a surface of the respective detection sample, and when the electron beam is irradiating one of the detection samples of rectangular parallelepiped shapes and one of that the electron beam scans or that the stage is moved is performed, at least one of the electron beam scanning amount and the stage movement amount is corrected with one of the scanning direction of the electron beam or the movement direction of the stage, in which the light detection time becomes the longest being defined as a reference direction, and when an electron beam is irradiated onto another of the detection samples in a rectangular parallelepiped shape, and one of that the electron beam is scanned or that the stage is moved is performed, at least one of the electron beam scanning direction and the stage movement direction is corrected so that the one of the scanning direction of the electron beam or the movement direction of the stage when the light detection time becomes the longest coincides with the reference direction.

13. A scanning electron microscope correction method for two-dimensionally scanning an electron beam with respect to a sample, and two-dimensionally detecting secondary electrons irradiated from the sample and reading a secondary electron image, wherein:

a detection sample is formed of a material that generates light of a single wavelength by being irradiated by the electron beam, the detection sample being formed in a substantially rectangular parallelepiped shape with a width that is almost equal to or smaller than a diameter of the electron beam in a transverse direction of the detection sample, one side face of two side faces of the detection sample being a reflection surface for reflecting the light of the single wavelength, the light that propagates within the detection sample and reaches the other side surface is detected at the other side surface, an actual irradiation position of the electron beam is detected based on the detected light intensity, and a scanning control amount of the electron beam is corrected so that a designated electron beam irradiation position coincides with the actual electron beam irradiation position.

* * * * *